(12) United States Patent
Friedman et al.

(10) Patent No.: US 11,406,805 B2
(45) Date of Patent: Aug. 9, 2022

(54) SYSTEMS AND METHODS FOR CROSS-LINKING TREATMENTS OF AN EYE

(71) Applicant: Avedro, Inc., Waltham, MA (US)

(72) Inventors: Marc D. Friedman, Needham, MA (US); Alexandra Nicklin, Cambridge, MA (US); Pavel Kamaev, Lexington, MA (US)

(73) Assignee: AVEDRO, INC., Waltham, MA (US)

( * ) Notice: Subject to any disclaimer, the term of this patent is extended or adjusted under 35 U.S.C. 154(b) by 182 days.

(21) Appl. No.: 16/324,489

(22) PCT Filed: Aug. 8, 2017

(86) PCT No.: PCT/US2017/045866
§ 371 (c)(1),
(2) Date: Feb. 8, 2019

(87) PCT Pub. No.: WO2018/031529
PCT Pub. Date: Feb. 15, 2018

(65) Prior Publication Data
US 2019/0192840 A1    Jun. 27, 2019

Related U.S. Application Data

(60) Provisional application No. 62/433,053, filed on Dec. 12, 2016, provisional application No. 62/372,290, filed on Aug. 8, 2016.

(51) Int. Cl.
*A61M 37/00* (2006.01)
*A61F 9/008* (2006.01)
(Continued)

(52) U.S. Cl.
CPC ............ *A61M 37/00* (2013.01); *A61F 9/007* (2013.01); *A61F 9/008* (2013.01); *A61F 9/0017* (2013.01);
(Continued)

(58) Field of Classification Search
CPC ............ A61M 2037/0007; A61M 5/00; A61M 35/00; A61M 37/0015; A61M 2037/0023;
(Continued)

(56) References Cited

U.S. PATENT DOCUMENTS 5,016,615 A    5/1991   Driller et al.
7,166,086 B2 * 1/2007   Haider ................ A61B 17/205
                                                          604/46
(Continued)

FOREIGN PATENT DOCUMENTS

EP    1707200 A1    10/2006
RU    2127099       3/1999
(Continued)

OTHER PUBLICATIONS

International Patent Application No. PCT/US2017/045866, International Search Report dated Feb. 15, 2018 (2 pages).
(Continued)

Primary Examiner — Nilay J Shah
(74) Attorney, Agent, or Firm — K&L Gates LLP

(57) ABSTRACT

Example eye treatments determine an area at a surface of a cornea for delivery of a cross-linking agent. The example treatments disrupt tissue at the area at the surface of the cornea up to a depth corresponding to apical layers of superficial squamous cells of the cornea, e.g., no greater than approximately 10 μm to approximately 15 μm. The example treatments apply a cross-linking agent to the area at the surface of the cornea. The cross-linking agent is transmitted through the disrupted area at a greater rate relative to non disrupted areas of the cornea. The example treatments deliver photoactivating light to the cornea. The photoactivating light activates the cross-linking agent to generate cross-linking activity in the cornea.

18 Claims, 7 Drawing Sheets

(51) Int. Cl.
*A61F 9/007* (2006.01)
*A61F 9/00* (2006.01)
*A61N 5/06* (2006.01)

(52) U.S. Cl.
CPC ...... *A61F 9/00802* (2013.01); *A61F 9/00804* (2013.01); *A61N 5/062* (2013.01); *A61F 2009/00844* (2013.01); *A61F 2009/00872* (2013.01); *A61F 2009/00893* (2013.01); *A61F 2009/00895* (2013.01); *A61M 2037/0007* (2013.01); *A61M 2037/0046* (2013.01); *A61M 2205/051* (2013.01); *A61M 2210/0612* (2013.01)

(58) Field of Classification Search
CPC .... A61M 2037/003; A61M 2037/0038; A61M 2037/0046; A61M 37/00; A61F 9/00763; A61F 9/013
See application file for complete search history.

(56) References Cited

U.S. PATENT DOCUMENTS

| | | | | |
|---|---|---|---|---|
| 8,784,363 | B2* | 7/2014 | Frederickson | A61M 5/158 604/46 |
| 2001/0041856 | A1 | 11/2001 | McDaniel | |
| 2004/0064087 | A1* | 4/2004 | Lastovich | A61M 37/00 604/46 |
| 2004/0077994 | A1* | 4/2004 | Lastovich | A61B 17/205 604/46 |
| 2006/0177430 | A1 | 8/2006 | Bhushan et al. | |
| 2006/0189964 | A1 | 8/2006 | Anderson et al. | |
| 2011/0054507 | A1 | 3/2011 | Batten et al. | |
| 2012/0289886 | A1* | 11/2012 | Muller | A61F 9/0079 604/20 |
| 2014/0249509 | A1 | 9/2014 | Rubinfield et al. | |
| 2017/0021021 | A1 | 1/2017 | Kamaev et al. | |
| 2017/0050044 | A1* | 2/2017 | Lebovitz | A61K 8/40 |

FOREIGN PATENT DOCUMENTS

| | | |
|---|---|---|
| RU | 2127100 | 3/1999 |
| WO | 2007/081750 A2 | 7/2007 |
| WO | 2012/004726 A1 | 1/2012 |
| WO | 2012/075409 A1 | 6/2012 |
| WO | 2012/158991 A2 | 11/2012 |
| WO | 2013/059837 A2 | 4/2013 |
| WO | 2013/148896 A1 | 10/2013 |

OTHER PUBLICATIONS

International Patent Application No. PCT/US2017/045866, Written Opinion of the International Searching Authority dated Feb. 15, 2018 (4 pages).

Sonoda S., "Gene Transfer to Corneal Epithelium and Keratocytes Mediated by Ultrasound with Microbubbles," Investigative Ophthalmology & Visual Science, vol. 47, No. 2, pp. 558-564; Feb. 2006 (7 pages).

* cited by examiner

SYSTEMS AND METHODS FOR CROSS-LINKING TREATMENTS OF AN EYE

This application is a National Stage Application of International Patent Application No. PCT/US2017/045866, filed Aug. 8, 2017, which claims the benefit of, and priority to, U.S. Provisional Patent Application No. 62/372,290, filed Aug. 8, 2016, and U.S. Provisional Patent Application No. 62/433,053, filed Dec. 12, 2016, the contents of these applications being incorporated entirely herein by reference.

BACKGROUND

Field

The present disclosure pertains to systems and methods for treating disorders of the eye, and more particularly, to systems and methods for cross-linking treatments of the eye.

Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

SUMMARY

Embodiments according aspects of the present disclosure include systems and methods for treating an eye. Example treatments determine an area at a surface of a cornea for delivery of a cross-linking agent. The example treatments disrupt tissue at the area at the surface of the cornea up to a depth corresponding to apical layers of superficial squamous cells of the cornea, e.g., no greater than approximately 10 µm to approximately 15 µm. The example treatments apply a cross-linking agent to the area at the surface of the cornea. The cross-linking agent is transmitted through the disrupted area at a greater rate relative to non-disrupted areas of the cornea. The example treatments deliver photoactivating light to the cornea. The photoactivating light activates the cross-linking agent to generate cross-linking activity in the cornea.

Correspondingly, an example system for enhancing permeability of an epithelium of a cornea includes a laser system configured to direct an ablative laser to a cornea of an eye. The example system also includes one or more controllers coupled to the laser system. The one or more controllers control the laser system to ablate tissue at an area at a surface of the cornea to a depth corresponding to apical layers of superficial squamous cells of the cornea, e.g., no greater than approximately 10 µm to approximately 15 µm. In some embodiments, the laser system may direct an excimer laser to the cornea.

Another example system for enhancing permeability of an epithelium of a cornea includes a housing. The example system includes a shaft having a proximal end and a distal end. The shaft is coupled to the housing at the proximal end and extends from the housing. The example system includes a disruption element coupled to the shaft at the distal end. The disruption element includes a disruption surface configured to contact the cornea and disrupt an area of the cornea. The example system includes a biasing element disposed between the housing and the disruption element. The biasing element applies a biasing force against the disruption element into contact with the cornea. In response to movement of the disruption element on the cornea, the disruption element disrupts the area of the cornea up to a depth corresponding to apical layers of superficial squamous cells of the cornea, e.g., no greater than approximately 10 µm to approximately 15 µm. In some embodiments, the disruption surface includes a pattern of micro-teeth. In other embodiments, the disruption element includes a sponge material.

DETAILED DESCRIPTION

Figure 1:
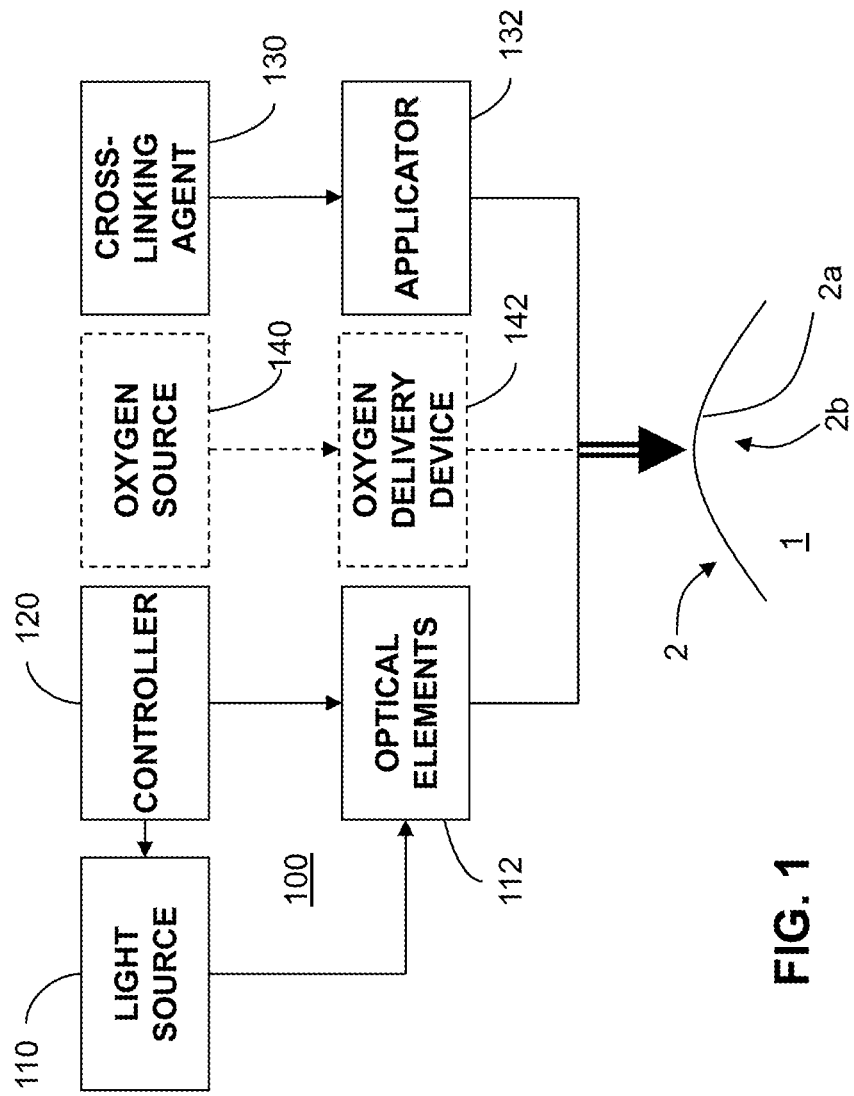
FIG. 1 illustrates an example system that delivers a cross-linking agent and photoactivating light to a cornea of an eye in order to generate cross-linking of corneal collagen, according to aspects of the present disclosure.

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the cross-linking agent 130 as drops to the cornea 2. Example systems and methods for applying the cross-linking agent is described in U.S. patent application Ser. No. 15/486,778, filed Apr. 13, 2017 and titled "Systems and Methods for Delivering Drugs to an Eye," the contents of which are incorporated entirely herein by reference.

The cross-linking agent 130 may be provided in a formulation that allows the cross-linking agent 130 to pass through the corneal epithelium 2a and to underlying regions in the corneal stroma 2b. Alternatively, the corneal epithelium 2a may be removed or otherwise incised to allow the cross-linking agent 130 to be applied more directly to the underlying tissue.

The treatment system 100 includes an illumination system with a light source 110 and optical elements 112 for directing light to the cornea 2. The light causes photoactivation of the cross-linking agent 130 to generate cross-linking activity in the cornea 2. For example, the cross-linking agent may include riboflavin and the photoactivating light may include ultraviolet A (UVA) (e.g., approximately 365 nm) light. Alternatively, the photoactivating light may include another wavelength, such as a visible wavelength (e.g., approximately 452 nm). As described further below, corneal cross-linking improves corneal strength by creating chemical bonds within the corneal tissue according to a system of photochemical kinetic reactions. For instance, riboflavin and the photoactivating light may be applied to stabilize and/or strengthen conical tissue to address diseases such as keratoconus or post-LASIK ectasia.

The treatment system 100 includes one or more controllers 120 that control aspects of the system 100, including the light source 110 and/or the optical elements 112. In an implementation, the cornea 2 can be more broadly treated with the cross-linking agent 130 (e.g., with an eye dropper, syringe, etc.), and the photoactivating light from the light source 110 can be selectively directed to regions of the treated cornea 2 according to a particular pattern.

The optical elements 112 may include one or more mirrors or lenses for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for photoactivating the cross-linking agent 130. In addition, the optical elements 112 may include one or more beam splitters for dividing a beam of light emitted by the light source 110, and may include one or more heat sinks for absorbing light emitted by the light source 110. The optical elements 112 may also accurately and precisely focus the photo-activating light to particular focal planes within the cornea 2, e.g., at a particular depths in the underlying region 2b where cross-linking activity is desired.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 mW/cm$^2$, larger irradiance of the photoactivating light, e.g., multiples of 5 mW/cm$^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the corneal surface 2A can be, for example, 5 J/cm$^2$, or as high as 20 J/cm$^2$ or 30 J/cm$^2$. The effective dose described can be delivered from a single application of energy, or from repeated applications of energy.

The optical elements 112 of the treatment system 100 may include a digital micro-mirror device (DMD) to modulate the application of photoactivating light spatially and temporally. Using DMD technology, the photoactivating light from the light source 110 is projected in a precise spatial pattern that is created by microscopically small mirrors laid out in a matrix on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Aspects of a dosimetry system are described in further detail below. Additionally, pre-clinical patient information may be combined with finite element biomechanical computer modeling to create patient specific pre-treatment plans.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than light of shorter wavelengths. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, the irradiance and the dose of photoactivating light affect the amount and the rate of cross-linking.

When the cross-linking agent 130 is riboflavin in particular, the UVA light may be applied continuously (continuous wave (CW)) or as pulsed light, and this selection has an effect on the amount, the rate, and the extent of cross-linking. If the UVA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 1 $mW/cm^2$ to approximately 1000 $mW/cm^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections, for instance, may involve combinations of myopia, hyperopia, astigmatism, irregular astigmatism, presbyopia and complex corneal refractive surface corrections because of ophthalmic conditions such as keratoconus, pellucid marginal disease, post-LASIK ectasia, and other conditions of corneal biomechanical alteration/degeneration, etc. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference.

The addition of oxygen also affects the amount of corneal stiffening. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of 07 is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal Cross-Linking with Pulsed Light," the contents of these applications being incorporated entirely herein by reference. Additionally, an example mask device for delivering concentrations of oxygen as well as photoactivating light in eye treatments is described in U.S. Provisional Patent Application Publication No. 2017/0156926, filed Dec. 3, 2016 and titled "Systems and Methods for Treating an Eye with a Mask Device," the contents of which are incorporated entirely herein by reference. For instance, a mask may be placed over the eye(s) to produce a consistent and known oxygen concentration above the surface.

When riboflavin absorbs radiant energy, especially light, it undergoes photoactivation. There are two photochemical kinetic pathways for riboflavin photoactivation, Type I and Type II. Some of the reactions involved in both the Type I and Type II mechanisms are as follows:

| Common reactions: | | | |
|---|---|---|---|
| $Rf \rightarrow Rf_1^*$, | I; | | (r1) |
| $Rf_1^* \rightarrow Rf$, | $\kappa 1$; | | (r2) |
| $Rf_1^* \rightarrow Rf_3^*$, | $\kappa 2$; | | (r3) |
| Type I reactions: | | | |
| $Rf_3^* + DH \rightarrow RfH^\bullet + D^\bullet$, | $\kappa 3$; | | (r4) |
| $2RfH^\bullet \rightarrow Rf + RfH_2$, | $\kappa 4$; | | (r5) |
| Type II reactions: | | | |
| $Rf_3^* + O_2 \rightarrow Rf + O_2^1$, | $\kappa 5$; | | (r6) |
| $DH + O_2^1 \rightarrow D_{ox}$, | $\kappa 6$; | | (r7) |
| $D_{ox} + DH \rightarrow D-D$, | $\kappa 7$; | CXL | (r8) |

In the reactions described herein, Rf represents riboflavin in the ground state. $Rf^*_1$ represents riboflavin in the excited singlet state. $Rf^*_3$ represents riboflavin in a triplet excited state. $Rf.^-$ is the reduced radical anion form of riboflavin. RfH. is the radical form of riboflavin. $RfH_2$ is the reduced form of riboflavin. DH is the substrate. $DH.^+$ is the intermediate radical cation. D. is the radical. $D_{ox}$ is the oxidized form of the substrate.

Riboflavin is excited into its triplet excited state $Rf^*_3$ as shown in reactions (r1) to (r3). From the triplet excited state $Rf^*_3$, the riboflavin reacts further, generally according to Type I or Type II mechanisms. In the Type I mechanism, the substrate reacts with the excited state riboflavin to generate radicals or radical ions, respectively, by hydrogen atoms or electron transfer. In Type II mechanism, the excited state riboflavin reacts with oxygen to form singlet molecular oxygen. The singlet molecular oxygen then acts on tissue to produce additional cross-linked bonds.

Oxygen concentration in the cornea is modulated by UVA irradiance and temperature and quickly decreases at the beginning of UVA exposure. Utilizing pulsed light of a specific duty cycle, frequency, and irradiance, input from both Type I and Type II photochemical kinetic mechanisms can be employed to achieve a greater amount of photochemical efficiency. Moreover, utilizing pulsed light allows regulating the rate of reactions involving riboflavin. The rate of reactions may either be increased or decreased, as needed, by regulating, one of the parameters such as the irradiance, the dose, the on/off duty cycle, riboflavin concentration, soak time, and others. Moreover, additional ingredients that affect the reaction and cross-linking rates may be added to the cornea.

If UVA radiation is stopped shortly after oxygen depletion, oxygen concentrations start to increase (replenish). Excess oxygen may be detrimental in the corneal cross-linking process because oxygen is able to inhibit free radical photopolymerization reactions by interacting with radical species to form chain-terminating peroxide molecules. The pulse rate, irradiance, dose, and other parameters can be adjusted to achieve a more optimal oxygen regeneration rate. Calculating and adjusting the oxygen regeneration rate is another example of adjusting the reaction parameters to achieve a desired amount of corneal stiffening.

Oxygen content may be depleted throughout the cornea, by various chemical reactions, except for the very thin corneal layer where oxygen diffusion is able to keep up with the kinetics of the reactions. This diffusion-controlled zone will gradually move deeper into the cornea as the reaction ability of the substrate to uptake oxygen decreases.

Riboflavin is reduced (deactivated) reversibly or irreversibly and/or photo-degraded to a greater extent as irradiance increases. Photon optimization can be achieved by allowing reduced riboflavin to return to ground state riboflavin in Type I reactions. The rate of return of reduced riboflavin to ground state in Type I reactions is determined by a number of factors. These factors include, but are not limited to, on/off duty cycle of pulsed light treatment, pulse rate frequency, irradiance, and dose. Moreover, the riboflavin concentration, soak time, and addition of other agents, including oxidizers, affect the rate of oxygen uptake. These and other parameters, including duty cycle, pulse rate frequency, irradiance, and dose can be selected to achieve more optimal photon efficiency and make efficient use of both Type I as well as Type II photochemical kinetic mechanisms for riboflavin photosensitization. Moreover, these parameters can be selected in such a way as to achieve a more optimal chemical amplification effect.

In addition to the photochemical kinetic reactions (r1)-(r8) above, however, the present inventors have identified the following photochemical kinetic reactions (r9)-(r26) that also occur during riboflavin photoactivation:

| | | |
|---|---|---|
| $Rf_3^* \to Rf$, | $\kappa 8$; | (r9) |
| $Rf_3^* + Rf \to 2RfH'$, | $\kappa 9$; | (r10) |
| $RfH_2 + O_2 \to RfH' + H^+ + O_2^-$, | $\kappa 10$; | (r11) |
| $RfH' + O_2 \to Rf + H^+ + O_2^-$, | $\kappa 11$; | (r12) |
| $2RfH_2 + O_2^- \to 2RfH' + H_2O_2$, | $\kappa 12$; | (r13) |
| $2RfH' + O_2^- \to 2Rf + H_2O_2$, | $\kappa 13$; | (r14) |
| $RfH' + H_2O_2 \to OH' + Rf + H_2O$, | $\kappa 14$ | (r15) |
| $OH' + DH \to D' + H_2O$, | $\kappa 15$; | (r16) |
| $D' + D' \to D - D$, | $\kappa 16$; | CXL (r17) |
| $O\frac{1}{2} \to O_2$, | $\kappa 18$; | (r18) |
| $D' + RfH_2 \to RfH' + DH$, | $\kappa 19$; | (r19) |
| $Rf + Rf \underset{\kappa_a^-}{\overset{\kappa_a^+}{\rightleftharpoons}} A_1$, | $\kappa_a = \kappa_a^+/\kappa_a^-$ | (r20) |
| $RfH_2 + RfH_2 \underset{\kappa_a^-}{\overset{\kappa_a^+}{\rightleftharpoons}} A_2$, | $\kappa_a = \kappa_a^+/\kappa_a^-$ | (r21) |
| $Rf + RfH_2 \underset{\kappa_b^-}{\overset{\kappa_a^+}{\rightleftharpoons}} A_3$, | $\kappa_b = \kappa_b^+/\kappa_b^-$ | (r22) |
| $Rf_1^* + A \to Rf + A$, | $\kappa_{1a}$ | (r23) |
| $Rf_3^* + A \to Rf + A$, | $\kappa_{3a}$ | (r24) |
| $2O_2^- \to O_2 + H_2O_2$, | $\kappa_{12}$ | (r25) |
| $OH° + CXL \to$ inert products, | $\kappa_{OH}$ | (r26) |

Figure 2A:
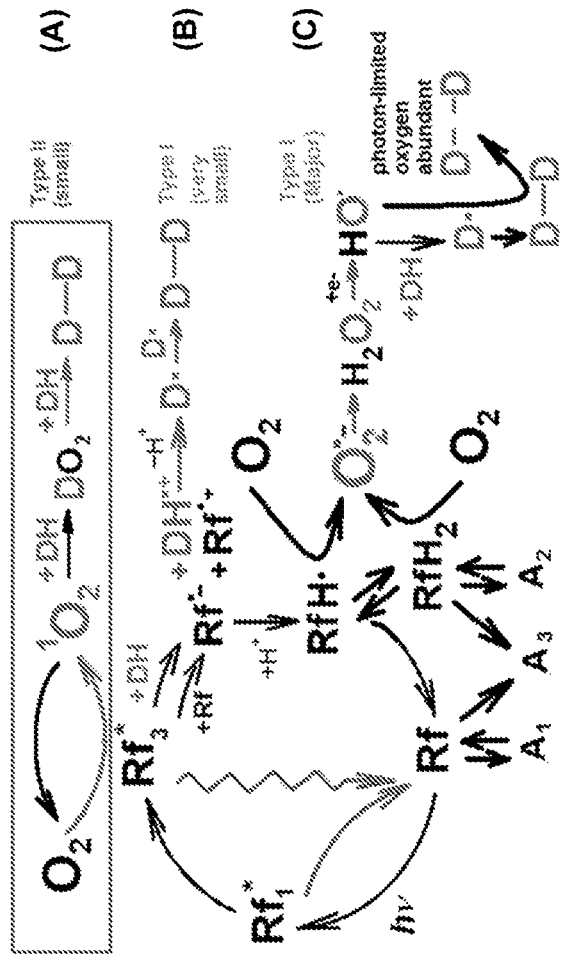
FIG. 2A illustrates a diagram for photochemical kinetic reactions involving riboflavin and photoactivating light (e.g., ultraviolet A (UVA) light) applied during a corneal cross-linking treatment, according to aspects of the present disclosure.

FIG. 2A illustrates a diagram for the photochemical kinetic reactions provided in reactions (r1) through (r26) above. The diagram summarizes photochemical transformations of riboflavin (Rf) under UVA photoactivating light and its interactions with various donors (DH) via electron transfer. As shown, cross-linking activity occurs: (A) through the presence of singlet oxygen in reactions (r6) through (r8) (Type II mechanism); (B) without using oxygen in reactions (r4) and (r17) (Type I mechanism); and (C) through the presence of peroxide ($H_2O_2$), superoxide ($O_2^-$), and hydroxyl radicals (.OH) in reactions (r13) through (r17).

As shown in FIG. 2A, the present inventors have also determined that the cross-linking activity is generated to a greater degree from reactions involving peroxide, superoxide, and hydroxyl radicals. Cross-linking activity is generated to a lesser degree from reactions involving singlet oxygen and from non-oxygen reactions. Some models based on the reactions (r1)-(r26) can account for the level of cross-linking activity generated by the respective reactions. For instance, where singlet oxygen plays a smaller role in generating cross-linking activity, models may be simplified by treating the cross-linking activity resulting from singlet oxygen as a constant.

All the reactions start from $Rf_3^*$ as provided in reactions (r1)-(r3). The quenching of $Rf_3^*$ occurs through chemical reaction with ground state Rf in reaction (r10), and through deactivation by the interaction with water in reaction (r9).

As described above, excess oxygen may be detrimental in corneal cross-linking process. As shown in FIG. 2A, when the system becomes photon-limited and oxygen-abundant, cross-links can be broken from further reactions involving superoxide, peroxide, and hydroxyl radicals. Indeed, in some cases, excess oxygen may result in net destruction of cross-links versus generation of cross-links.

As described above, a large variety of factors affect the rate of the cross-linking reaction and the amount of biomechanical stiffness achieved due to cross-linking. A number of these factors are interrelated, such that changing one factor may have an unexpected effect on another factor. However, a more comprehensive model for understanding the relationship between different factors for cross-linking treatment is provided by the photochemical kinetic reactions (r1)-(r26) identified above. Accordingly, systems and methods can adjust various parameters for cross-linking treatment according to this photochemical kinetic cross-linking model, which provides a unified description of oxygen dynamics and cross-linking activity. The model can be employed to evaluate expected outcomes based on different combinations of treatment parameters and to identify the combination of treatment parameters that provides the desired result. The parameters, for example, may include, but are not limited to: the concentration(s) and/or soak times of the applied cross-linking agent; the dose(s), wavelength(s), irradiance(s), duration(s), and/or on/off duty cycle(s) of the photoactivating light; the oxygenation conditions in the tissue; and/or presence of additional agents and solutions.

Figure 2B:
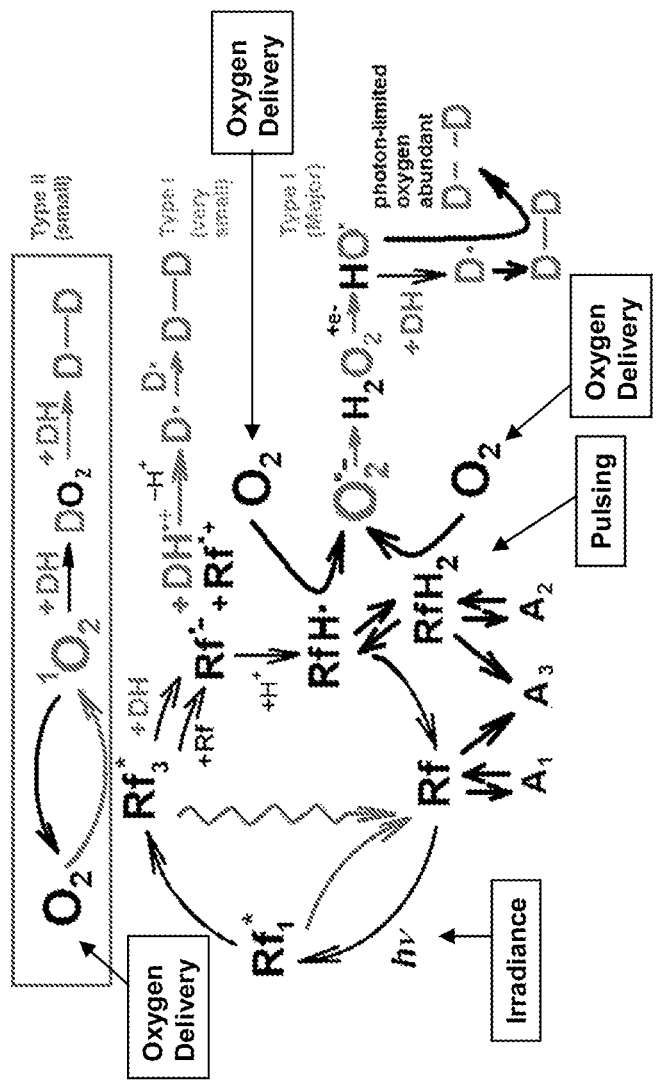
FIG. 2B illustrates a diagram for parameters that can affect the photochemical kinetic reactions shown in FIG. 2A.

As shown in FIG. 2B, aspects of the system of reactions can be affected by different parameters. For instance, the irradiance at which photoactivating light is delivered to the system affects the photons available in the system to generate $Rf_3^*$ for subsequent reactions. Additionally, delivering greater oxygen into the system drives the oxygen-based reactions. Meanwhile, pulsing the photoactivating light affects the ability of the reduced riboflavin to return to ground state riboflavin by allowing additional time for oxygen diffusion. Of course, other parameters can be varied to control the system of reactions.

Further aspects of the photochemical kinetic reactions provided in reactions (r1)-(r26) are described in U.S. Patent Application Publication No. 2016/0310319, filed Apr. 27, 2016 and titled "Systems and Methods for Cross-Linking Treatments of an Eye," the contents of which are incorporated entirely herein by reference.

When light of a particular wavelength is applied to a cross-linking agent, such as riboflavin, the light can excite the cross-linking agent and cause the cross-linking agent to fluoresce. As such, an excitation light can be employed to cause a cross-linking agent in corneal tissue to fluoresce and determine how the cross-linking agent is distributed in the corneal tissue. When an image of the cornea is taken during the application of the excitation light, the intensity (magnitude) of the fluorescence, for instance, can be measured to determine the amount, i.e., dose, of cross-linking agent taken up by the corneal tissue. Using these principles, dosimetry systems can determine the presence and distribution of the cross-linking agent in the cornea by capturing one or more images of the fluorescence from the cross-linking agent as it responds to the excitation light. Further aspects of a dosimetry system, particularly employing hyperspectral analysis of fluorescence, are described in U.S. Patent Application Publication No. 2016/0338588, filed May 23, 2016 and titled "Systems and Methods for Monitoring Cross-Linking Activity for Corneal Treatments," the contents of which are incorporated entirely herein by reference.

In general, the structure of the cornea includes five layers. From the outer surface of the eye inward, these are: (1) epithelium, (2) Bowman's layer, (3) stroma, (4) Descemet's membrane, and (5) endothelium. During example cross-linking treatments, the stroma is treated with riboflavin, a photosensitizer, and ultraviolet (UV) light is delivered to the cornea to activate the riboflavin in the stroma. Upon absorbing UV radiation, riboflavin undergoes a reaction with oxygen in which reactive oxygen species and other radicals are produced. These reactive oxygen species and other radicals further interact with the collagen fibrils to induce covalent bonds that bind together amino acids of the collagen fibrils, thereby cross-linking the fibrils. The photo-oxidative induction of collagen cross-linking enhances the biomechanical strength of the stoma, and can provide therapeutic benefits for certain ophthalmic conditions, such as keratoconus, or generate refractive changes to correct myopia, hyperopia and/or astigmatism.

As the outermost barrier of the cornea, the epithelium protects the cornea from bacteria and the free flow of fluids into the stroma. The epithelium is formed from several layers of cells. The innermost layer is the basal epithelial layer, which includes a single layer of columnar basal cells that adheres to Bowman's layer of the stroma. The basal epithelial layer is then followed by two to three superbasal epithelial layers, which includes wing cells that are polyhedral in shape. The superbasal epithelial layers are followed by two to three apical layers of superficial squamous cells with flat nuclei. The superbasal squamous layers are covered by a tear film, which is a lipid, aqueous and mucous film. The tight junctions formed by edge-to-edge contact by the superficial squamous cells allow the epithelium to act as an effective barrier. The layers of the epithelium are constantly undergoing mitosis. The life cycle of these epithelial cells starts with the basal cells maturing to wing cells, which mature to squamous cells, which then age and slough off into the tear film.

The epithelium functions to regulate nutrients, including oxygen, that are admitted into the stromal tissue from the tear film. This regulation is carried out via the epithelium's physiological "pumps" that are driven by osmotic pressure across the epithelium due to differential concentrations of barrier-permeable solutes on either side of the epithelium. When healthy, certain nutrients in the tear film that become depleted within the stroma can permeate the epithelium via osmotic pressure to resupply the stroma. However, while oxygen and some other small molecule nutrients can reach the stroma according to this mechanism, certain photosensitizers cannot pass through the epithelium.

Riboflavin, for example, is a relatively large, hydrophilic molecule that cannot penetrate the tight junctions of the epithelium. The epithelium slows the amount of riboflavin that can penetrate the stroma. Thus, a variety of approaches have been employed to overcome low riboflavin diffusivity and deliver sufficient concentrations of riboflavin to the stroma for performing corneal cross-linking treatments. According to one approach, the epithelium is removed (epithelium debridement) before a riboflavin solution is applied directly to the stroma. Although removing the epithelium allows riboflavin to reach the stroma, the approach is associated with patient discomfort, risks of infection, and other possible complications.

Meanwhile, other approaches avoid epithelial debridement. For example, riboflavin may be provided in a formulation that allows the cross-linking agent to pass through the epithelium. Such formulations are described, for example, in U.S. Patent Application Publication No. 2010/0286156, filed on May 6, 2009 and titled "Collyrium for the Treatment of Conical Cornea with Cross-Linking Trans-Epithelial Technique, and in U.S. Patent Application Publication No. 2013/0267528, filed on Jan. 4, 2013 and titled "Trans-Epithelial Osmotic Collyrium for the Treatment of Keratoconus," the contents of these applications being incorporated entirely herein by reference. In particular, some riboflavin formulations include ionic agents, such as benzalkonium chloride (BAC), with a specific osmolarity of sodium chloride (NaCl). Although such formulations may enhance permeability of the epithelium, they are disadvantageously corrosive to the epithelium, beyond the tight junctions.

Additionally or alternatively, another solution and/or mechanical forces may be applied to enhance the permeability of the epithelium and allow the riboflavin to pass more easily through the epithelium. Examples of approaches for enhancing or otherwise controlling the delivery of a cross-linking agent to the underlying regions of the cornea are described, for example, in U.S. Patent Application Publication No. 2011/0288466, filed Apr. 13, 2011 and titled "Systems and Methods for Activating Cross-Linking in an Eye," and U.S. Patent Application Publication No. 2012/0289886, filed May 18, 2012 and titled "Controlled Application of Cross-Linking Agent," the contents of these applications being incorporated entirely herein by reference.

According to aspects of the present disclosure, systems and methods enhance the permeability of the epithelium by disrupting (e.g., removing) only the two to three apical layers of superficial squamous cells, which form the tight junctions for the barrier function of the epithelium. Such disruption allows para-cellular drug delivery to proceed unhindered. This approach may be referred to as Trans-Epithelial Apicalectomy (TEATM) or Apical Epithelial Debridement (AED) or Partial Epithelial Debridement or Disruption (PED). With this approach rapid uptake of photosensitizer (e.g., cross-linking agent) formulations in the stroma can be achieved without using corrosive additives, such as BAC. This effective drug delivery allows acute focal treatment of ocular disease or refractive disorders with the photosensitizer formulations.

As described above, a large variety of factors affect the rate of the cross-linking reaction and the amount of biomechanical stiffness achieved due to cross-linking. Indeed, enhancing permeability through the disruption of the apical layers to deliver high concentrations of cross-linking agent to the stroma is only one aspect of achieving efficient cross-linking Thus, such permeability enhancement may also be combined with the use of specific cross-linking agent formulations as well as oxygen.

Figure 3:
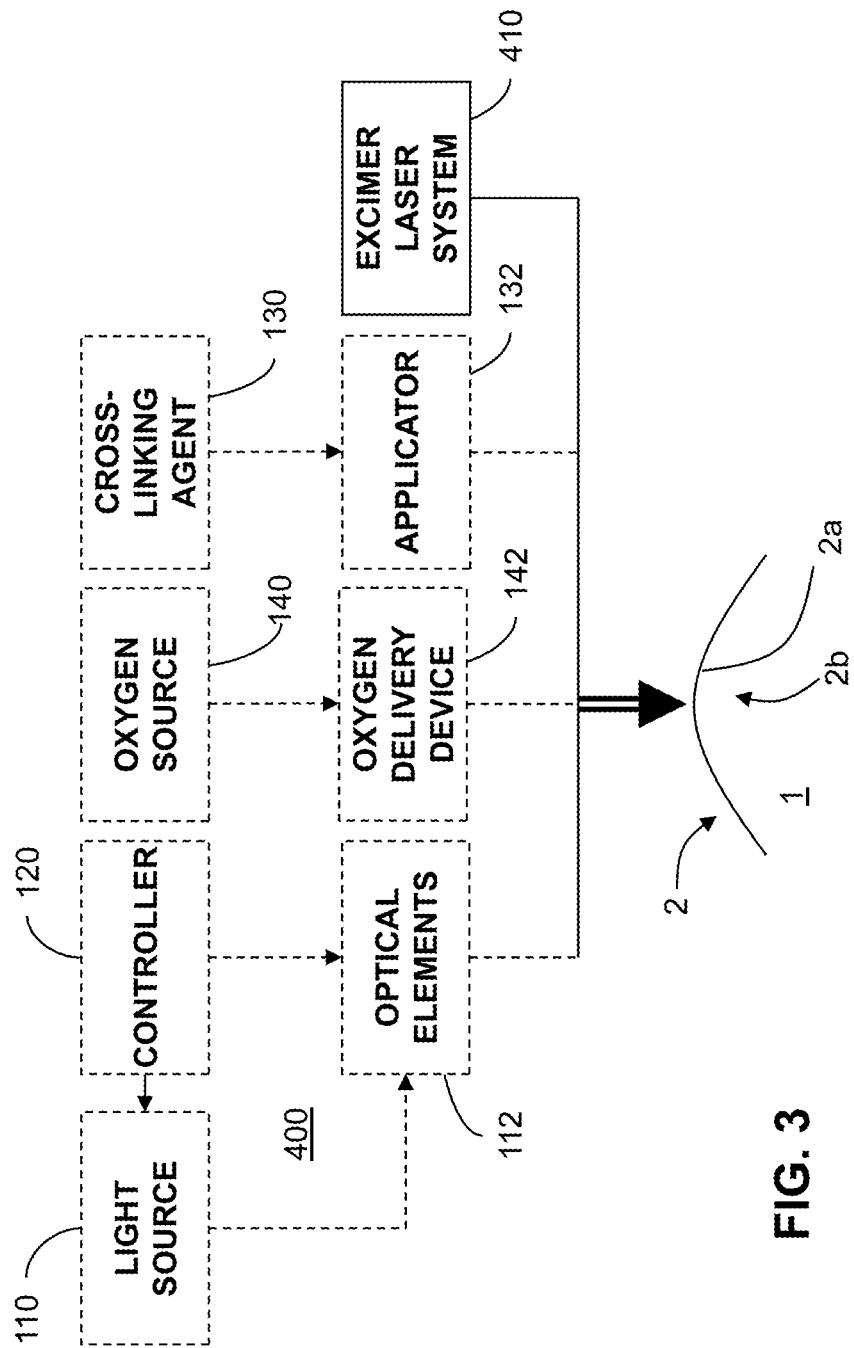
FIG. 3 illustrates an example treatment system for disrupting the apical layers of superficial squamous cells, according to aspects of the present disclosure.

As illustrated in FIG. 3, an example treatment system 400 includes an excimer laser system 410 in addition to one or more of the elements of the example treatment system 100 described above. In particular, the treatment system 400 may include an illumination system with the light source 110 and the optical elements 112 to direct photoactivating light (e.g., UVA light) to the cornea. The treatment system 400 may include one or more controllers 120 that control aspects of the treatment system 400, including operation of the excimer laser system 410 as described herein. The treatment system 400 may include the applicator 132 for applying the cross-linking agent 130 to the cornea 2. The treatment system 400 may include an oxygen delivery system with the oxygen source 140 and the oxygen delivery device 142 to deliver oxygen at a selected concentration to the cornea 2.

The excimer laser system 410 may be controlled by the one or more controllers 120 to ablate an area of the cornea with a depth corresponding to the apical layers of superficial squamous cells. For instance, the depth may be no greater than approximately 10 µm to approximately 15 µm. The cells may be disrupted according to a pattern just slightly larger than the desired pattern of cross-linking activity in the cornea 2. Advantageously, the use of the excimer laser system 410 can achieve precise disruption of the apical layers and provide more consistent results than some approaches that involve manual disruption by a practitioner.

After disruption by the excimer laser system 410, a riboflavin formulation is applied via the applicator 132 to the eye for a given soak period (though alternative photosensitizers may be employed). For instance, the riboflavin formulation may be applied according to the drug delivery systems and methods described in U.S. patent application Ser. No. 15/486,778, filed Apr. 13, 2016 and titled "Systems and Methods for Delivering Drugs to an Eye," referenced above. The riboflavin formulation may be specifically formulated to be hypotonic and may have additional trace additives such as EDTA (a Ca+2 Chelator) to open up any additional calcium channels that may still be present. The concentration of EDTA falls in specific ranges so as to open up the channels but not so much as to quench riboflavin absorption. The soak period may also be monitored using fluorescence dosimetry. To photoactivate the riboflavin, the illumination system may deliver UVA light of a specified dose to the treated cornea as described above. The oxygen delivery system may also deliver concentrations of oxygen to the eye.

Advantageously, the example treatment system 400 can increase the precision of the treatment by substantially confining the treatment area and drug delivery to the pattern of ablation applied by the excimer laser system 410. The excimer laser system 410 can have a cut depth precision of approximately 0.25 µm to approximately 0.5 µm and can produce a very smooth surface. Because riboflavin does not penetrate the stroma as effectively outside the pattern of ablation defined by the excimer laser system, the dose of riboflavin is confined to the stroma.

In the area treated by the excimer laser system 410, the thinner epithelium retains less residual riboflavin which can absorb UVA photons from the illumination system. This increases cross-linking photon efficiency as more photons make it to the stroma rather than being absorbed at the epithelium, and when oxygen is applied, higher oxygen concentration occurs at Bowman's layer based on Fick's Law of Diffusion.

The use of the example treatment system 400 may also provide healing benefits. For instance, cytotoxicity to surrounding tissues may be reduced or eliminated as compared to treatments that enhance epithelial permeability by applying BAC. There may also be less hyperplasia as compared to treatments that employ BAC, because the underlying wing and basal cells remain undamaged thereby reducing the level of cytokine release and eliminating epithelial slough. Infection risk may also be reduced as compared to full debridement, because only two to three cell layers are disrupted. Furthermore, the wing cells can differentiate into squamous cells very quickly to reform the tight junctions which provide the barrier function. Additionally, there may be less short-term discomfort because the focal treatment affects a smaller area and most of the nerve fiber endings remain intact.

Figure 4A:
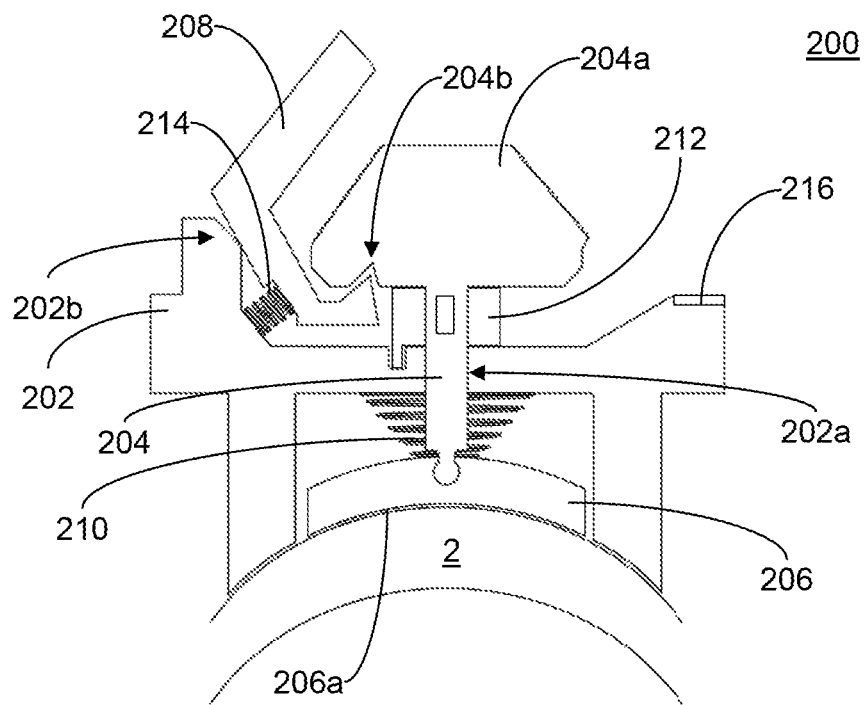
FIG. 4A illustrates an example device for disrupting the apical layers of superficial squamous cells, according to aspects of the present disclosure.

Although the excimer laser system 410 described above may be effective in disrupting the apical layers of superficial squamous cells, other techniques may be employed. According to some embodiments, other types of laser systems (e.g., a femtosecond laser system) may be employed. According to a further embodiment, FIG. 4A illustrates an example device 200 for mechanically disrupting the apical layers according to another approach. The device 200 may be referred to as a mechanical apical epithelial disruptor device. Like the excimer laser system 410, the device 200 may be employed with one or more of the elements of the example treatment system 100 described above.

The device 200 includes an outer housing 202 that combines and arranges the various device components. A practitioner can manipulate and hold the outer housing 202 in place to disrupt the apical layers. The device 200 includes a winding shaft 204, which passes through an aperture 202a of the outer housing 202. The winding shaft 204 has a knurled knob 204a disposed at a proximal end of the winding shaft 204. The knurled knob allows a practitioner to wind the winding shaft 204. A release lever 208 with a fulcrum 202b on the outer housing 202 engages the winding shaft 204 at an indent 204b. The device 200 also includes a disruptor insert 206 that is coupled to a distal end of the winding shaft 204 and is pressed into contact with the cornea 2.

The device 200 includes a torsion spring 212 which is disposed about the winding shaft 204. The torsion spring 212 is coupled to the winding shaft 204 and the outer housing 202 with a spring capture feature. As the winding shaft 204 is wound through a specific angle of rotation (e.g., approximately 90 degrees), via the knurled knob 204a, the torsion spring 212 correspondingly applies an opposing rotative force to the winding shaft 204. However, if the release lever 208 remains engaged with the indent 204b, the release lever 208 prevents the winding shaft from rotating in response to the rotative force applied by the torsion spring 212. The device 200 additionally includes a lever tensioning spring 214 that applies a biasing force between the outer housing 202 and the release lever 208.

The device 200 includes a spring 210 (e.g., constant force spring) that acts between the outer housing 202 and the disruptor insert 206. Although FIG. 4A may illustrate the spring 210 as a helical spring, other biasing elements may be employed in alternative embodiments to apply a biasing force to the disruptor insert 206. The force from the spring 210 causes the disruptor insert 206 to press against the cornea 2. The disruptor insert 206 has a contoured bottom surface 206a that combines with the force from the spring 210 to applanate the corneal surface. The contoured bottom surface 206a may have any of various radii of curvature and/or other shape features for desired contact with the corneal surface.

Figures 4B, 4C, 4D:
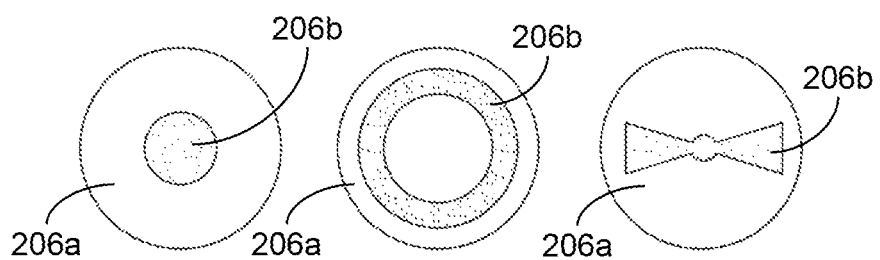
FIG. 4B illustrates an example disruptor pattern for treating myopia with the example device of FIG. 3A.
FIG. 4C illustrates another example disruptor pattern for treating hyperopia with the example device of FIG. 3A.
FIG. 4D illustrates another example disruptor pattern for treating astigmatism with the example device of FIG. 3A.

The bottom surface 206a of the disruptor insert 206 includes a pattern of micro-teeth 206b (shown in FIGS. 4B-D). When the disruptor insert 206 presses against the corneal surface, the micro-teeth 206b penetrate the corneal epithelium for a depth which corresponds to the apical layers of superficial squamous cells that are to be disrupted to enhance permeability. For instance, the depth may be no greater than approximately 10 µm to approximately 15 µm.

The micro-teeth 206b may have various patterns, tooth sizes, tooth shapes, and tooth distributions. For instance, FIG. 4B illustrates an example disruptor pattern for treating myopia. FIG. 4C illustrates an example disruptor pattern for treating hyperopia. FIG. 4D illustrates an example disruptor pattern for treating astigmatism. Various manufacturing methods may be employed to form the micro-teeth 206b, including but not limited to stamping, injection molding, photolithography, and/or any combination thereof.

When the release lever 208 is manually released from the indent 204b by the practitioner, the winding shaft 204 can unwind in response to the rotative force applied by the torsion spring 212. With the disruptor insert 206 pressed against the corneal surface, the bottom surface 206a with the micro-teeth 206b correspondingly rotates against the corneal surface. The micro-teeth 206b cause a disruption of the apical layers of superficial squamous cells according to the pattern of the micro-teeth 206b.

The entire device 200 may be configured to be a disposable single-use device. Alternatively, the entire device 200 may be sterilizable and reusable. In the latter case, the device 200 may be customized for each use by replacing the disruptor insert 206 with one having a desired pattern, tooth size, tooth shape, tooth distribution, etc. As such, the disruptor inserts 206 may be configured as disposable single-use devices.

Advantageously, the constant force spring 210 helps the disruptor insert 206 to apply a consistent force to every patient no matter who the practitioner is. In other words, the constant force spring 210 allows the results of using the device 200 to be less dependent on manual operation by the practitioner. Nevertheless, to enhance repeatability, rotation of the disruptor insert 206 may be limited to a specific number of degrees.

In an example implementation of the device 200, the practitioner holds the outer housing 202 in one hand and then rotates the knurled knob 204a for a specified rotation until the indent 204b aligns with the release lever 208 and the lever release arm 208 clicks into engagement with the indent 204b via the lever tensioning spring 214. The practitioner then holds the outer housing 202 (e.g., in his/her dominant hand) and aligns the outer housing 202 with the patient's eye both in the vertical and horizontal planes. The device 200 may be centered on the pupil and/or limbus. Additionally, the rotation of the winding shaft 204 may be aligned to an angle based on any astigmatism. For instance, an astigmatic axis indicator 216 may include holes in the outer housing 202 for alignment. Alternatively, aspects of the outer housing 202 and the disruptor insert 206 may be formed from a translucent material (e.g., plastic or glass) to allow for visualization. The practitioner presses the outer housing 202 against the surface of the eye. This produces proper applanation of the corneal surface by the disruptor insert 206 with a known amount of applanation force provided by the constant force spring 210. The practitioner then releases the release lever 208 (e.g., by pressing the release lever 208 with his/her index finger) to allow the disruptor insert 206 to rotate with the unwinding of the winding shaft 204. Accordingly, the device 200 can be operated with one hand. Advantageously, the design of the device 200 generates a uniform disruption of the apical epithelium that is less dependent on the practitioner.

Figure 5A:
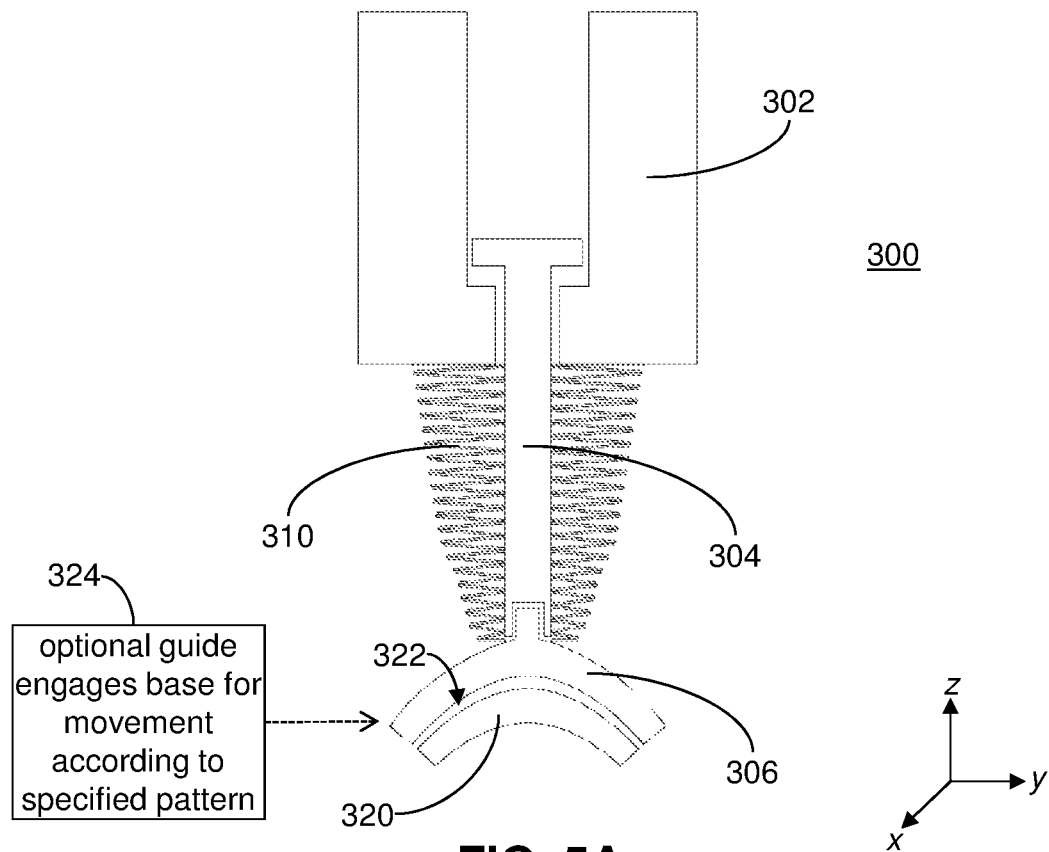
FIG. 5A illustrates another example device for disrupting the apical layers of superficial squamous cells, according to aspects of the present disclosure.
Figure 5B:
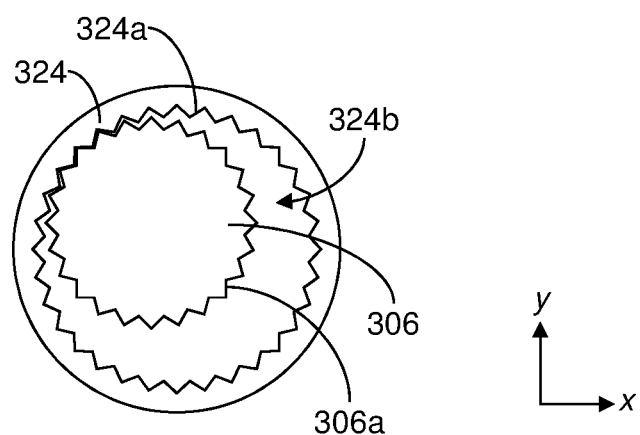
FIG. 5B illustrates an example implementation of the example device shown in FIG. 5A, according to aspects of the present disclosure.

FIGS. 5A-B illustrate another example device 300 for mechanically disrupting the apical layers. Similar to the device 200 above, the device 300 includes an outer housing 302 and a spring 310 (e.g., constant force spring). In place of the disruptor insert 206, however, the device 300 employs a sponge (or similar) material 320 with given porosity, stiffness, and desired hydrophilic/lipophilic properties. The sponge material 320 may be attached to a base 306, e.g., via an adhesive 322, and the combination of the sponge material 320 and the base 306 may be provided as a sterile, disposable sub-assembly that snaps into a shaft 304 of the device 300. The ability to dispose of the sub-assembly and reuse the remaining components of the device 300 reduces waste.

In some aspects, the device 300 may be simpler to operate than the device 200. The practitioner holds the outer housing 302 and presses the device 300 against the cornea. Rather than employing the winding shaft 204 described above to rotate the sponge material 320 automatically, the practitioner manually moves the device 300 in an orbital motion for a prescribed number of rotations and/or in a linear back-and-forth motion (left-right, up-down, etc.) perpendicular to the radius of curvature a prescribed number of times. Because the sponge material 320 is contoured to match the shape of the cornea and the spring 210 applies a constant force to the corneal surface, a given porosity and stiffness of sponge creates a repeatable amount of rubbing of the corneal surface. Although the use of the device 300 may be more dependent on the practitioner, the device 300 reduces any variability over a free form rubbing of the surface with a sponge.

The sponge material 320 may be dry or wetted with saline or a specified solution. For instance, the specified solution may include proparacaine, a low concentration solution containing an agent such as BAC, or a specific viscosity lubricant using hydroxypropyl methyl cellulose (HPMC) for instance.

The device 300 may be employed with a guide 324 that movably engages the base 306. The guide 324 allows the practitioner to move the device 300 more precisely according to a specified pattern. In particular, the guide 324 allows the base 306 to move and ride/follow along one or more sides of the guide 324. Guides 324 of various shapes can be employed to provide various patterns of rubbing by the device 300.

During operation, the practitioner holds the guide 324 in a fixed position while the device 300 is moved relative to the guide 324. As shown in the example implementation of FIG. 5B, the guide 324 may have a circular opening 324b and the device 300 may be positioned within the circular opening 324b. The base 306 of the device 300 may include teeth 306a that engage corresponding teeth 324a arranged along the inner edge of the circular opening 324b of the guide 324. With the teeth 306a, 324a engaged, the practitioner can roll the device 300 along the inner edge of the circular opening 324b so that the device 300 moves in a circle defined by the circular opening 324b. This circular movement determines the pattern of rubbing by the device 300. Although the pattern in FIG. 5B may be circular, other patterns (e.g., elliptical) may be employed. Moreover, more than one guide 324 may be employed to apply more than one pattern for a treatment.

In some embodiments, the base 306 and the guide 324 may be configured so that the teeth 306a, 324a engage each other in a manner similar to tapered gears. Such a configuration may help the practitioner to follow the guide 324 more stably and to maintain perpendicularity to the corneal surface while the device 300 moves. The angle of the taper is derived from the size of the guide 324 and the average distance the device 300 is held away from the eye. The configuration may accommodate the deepest possible eye socket.

Therefore, embodiments according to the present disclosure enhance epithelial permeability for treatments with agents, such as riboflavin. Correspondingly, example eye treatments determine an area at a surface of a cornea for delivery of a cross-linking agent. The example treatments disrupt tissue at the area at the surface of the cornea up to a depth corresponding to apical layers of superficial squamous cells of the cornea. The disruption of the epithelial tissue may occur at a depth of no greater than approximately 10 μm to approximately 15 μm. In other embodiments, effective disruption may occur at different depths, e.g., at a depth up to approximately 25 μm. The example treatments apply the cross-linking agent to the area at the surface of the cornea. The cross-linking agent is transmitted through the disrupted area at a greater rate relative to non-disrupted areas of the cornea. The example treatments deliver photoactivating light to the cornea. The photoactivating light activates the cross-linking agent to generate cross-linking activity in the cornea.

As described above, disrupting the tissue at the area at the surface of the cornea may involve ablating the area with the excimer laser system 410. Alternatively, disrupting the tissue at the area at the surface of the cornea may involve moving a disruption element over the surface of the cornea, where the disruption element includes a disruption surface configured to contact the cornea and disrupt the tissue at the area at the surface of the cornea. As used herein, a disruption surface may refer to a surface that is sufficiently non-smooth or abrasive to apply frictional and/or shear forces that can remove epithelial tissue from a cornea. For instance, such surfaces can include protrusions, such as the micro-teeth 206b described above, or such surfaces may include pores or depressions as provided by the sponge material 320 described above.

Additional or alternative approaches for disrupting epithelial tissue (e.g., apical layers of superficial squamous cells) include, but are not limited to:

Applying a fluid jet to the eye. One or more fluid jets of given shape(s) may be guided over the surface of the eye to disrupt the epithelial tissue according to a desired pattern. The given shape(s) may be defined by different diameters, widths, etc. The fluid may be water. Alternatively, the fluid may have a formulation that promotes disruption of the epithelial tissue. For instance, the fluid may include agent(s) that enhance epithelial permeability, such as those described above (e.g., ionic agent) or in U.S. Patent Application Publication No. U.S. 2017/0021021, filed Jul. 21, 2016 and titled "Systems and Methods for Treatments of an Eye with a Photosensitizer, the contents of which are incorporated entirely herein by reference (e.g., non-ionic agent). To achieve a specific amount of epithelial disruption/permeability enhancement. The fluid jets may be delivered according to any combination of parameters. For instance, each fluid jet may provide a continuous stream or pulses with specified pressure, velocity, and duration. Pulses may have specified duty cycle and duration.

Applying an applicator tipped with cotton or similar material. Rather than employing a sponge (or similar) material as described above, an applicator may employ cotton or similar material to rub and disrupt the epithelial tissue.

Applying an anesthetic during preparation and/or soak and/or irradiation steps of a treatment.

Applying a femtosecond laser. A femtosecond laser system may be employed to drill a specific pattern of holes in the epithelium. Alternatively, a femtosecond laser system may be applied to achieve uniform surface ablation/disruption of at a depth corresponding to the apical layers of superficial squamous cells. For instance, the depth may be no greater than approximately 10 μm to approximately 15 μm.

Applying microneedles. Microneedle(s) may be employed to disrupt the epithelium as well as to inject drugs, etc.

Applying a Goldmann applanator. A Goldmann applanator may be soaked with a chemical disruptor as described above and applied to the eye.

Applying heat energy and/or ultrasound. Heat energy and/or ultrasound may be applied to modify the corneal structure and increase its permeability. Aspects of such application are described, for instance, in U.S. Patent Application Publication No. 2011/0288466 and U.S. Patent Application Publication No. 2012/0289886 as referenced above.

Providing regularized epithelial scoring with various epithelial disruptor tools.

Figure 6:
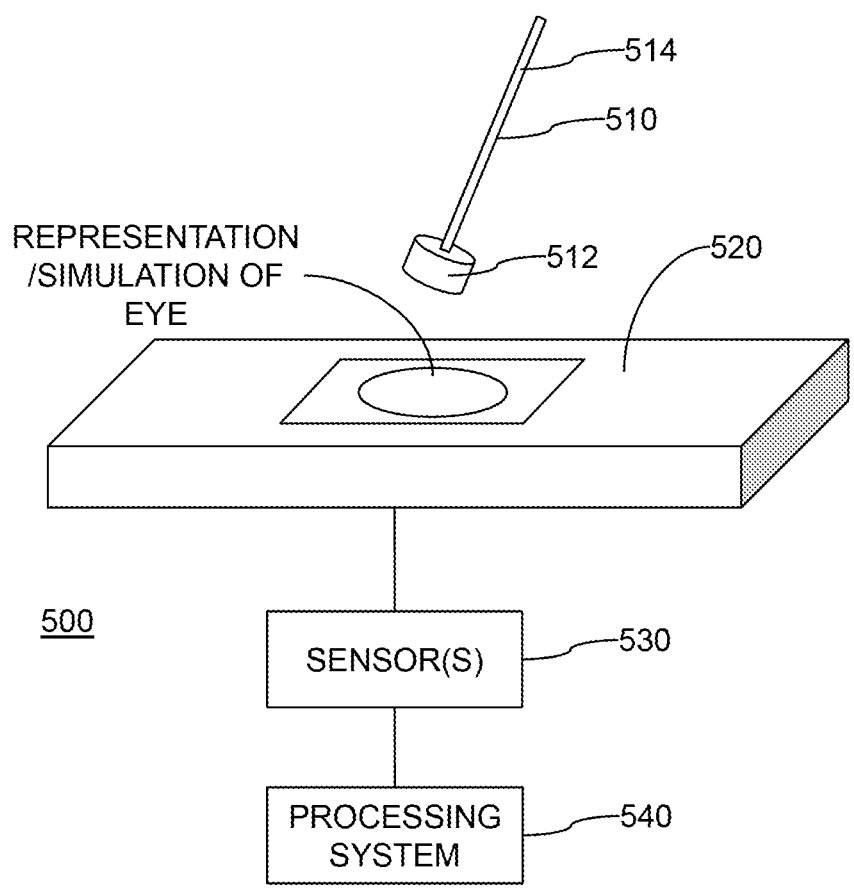
FIG. 6 illustrates an example system for evaluating and/or optimizing a manual technique for disrupting epithelial tissue, according to aspects of the present disclosure.

Although the embodiments described herein eliminate or reduce the dependence on the practitioner when disrupting epithelial tissue, results for some approaches may vary according to practitioner technique. FIG. 6 illustrates an example system 500 for improving practitioner technique so that disruption of epithelial tissue can be achieved with consistent results. For instance, practitioners can use the example system 500 to train or practice with an applicator 510 that rubs the corneal surface with a tip 512 formed from sponge, foam, cotton, or similar material on the end of a stylus 514. The example system 500 can also provide training for other disruption devices, such as the example devices 200, 300 described above.

The example system 500 includes a surface 520 that the practitioner can contact with the tip 512 of the applicator 510. In particular, with the surface 520, the practitioner can simulate using the applicator 510 to disrupt epithelial tissue on an actual corneal surface. As shown in FIG. 6, the surface 520 may be a touch pad. The surface 520 may provide an image that represents the eye, including size and shape. In some embodiments, the surface 520 may simulate characteristics of a cornea, such as the texture of the corneal surface, shape of the cornea, stiffness of the corneal tissue, etc.

The example system 500 also includes one or more sensors 530 that can measure or otherwise determine aspects of the practitioner technique, e.g., how the practitioner strokes the applicator 510 against the surface 520. During simulation by the practitioner, the one or more sensors 530 can determine: number of strokes from the applicator 510, direction of the strokes, speed of the strokes, starting and ending acceleration of the strokes, pressure of the strokes, variations in the pressure of the strokes, pressure-distance profile of the strokes, variations in the pressure-distance profile of the strokes, the area covered by the strokes, the angle between the stylus 514 of the applicator 510 and the surface 520, and/or other characteristics of the practitioner technique.

Examples of sensors 530 may include one or more mechanical sensors, pressure sensors, multi- or single-axis load cells/strain gauges, inductive sensors, visual or optical sensors, conductivity sensors, piezometer/piezoelectric sensors, force gauges, capacitive sensors, gyroscopic sensors, velocity and/or acceleration sensors, acoustic sensors, torque sensors, hall effect sensors, and/or other types of sensors. Some sensors 530 may be integrated with the surface 520. For instance, some sensors 530 may be arranged in arrays in a flat panel detector or along the surface 520. Other sensors 530 may be integrated into the applicator 510. Meanwhile, other sensors 530 may be separate from the surface 520 and the applicator 510.

The one or more sensors 530 may be communicatively coupled to a processing system 540 that can receive data from the sensors, evaluate the data, and provide feedback to the practitioner on his/her technique. The feedback may be communicated visually via a graphic display and/or aurally via speakers. In some embodiments, the processing system 540 may be combined with the surface 520 to provide a more integrated system 500. In other embodiments, the processing system 540 may be a computing device coupled by a wired or wireless connection. In further embodiments, the example system 500 may include, or be further coupled to, other equipment to simulate the manual procedure.

The feedback from the processing system 540 may provide a simple pass/fail indicator. Alternatively or additionally, the feedback may provide information regarding the precision, accuracy, variations, and completeness of the practitioner technique. Alternatively or additionally, the feedback may provide the detailed data from the one or more sensors 530. The feedback may also suggest how the practitioner technique may be improved to achieve more effective disruption of the epithelial tissue. The feedback may be customized according to different types of procedures that involve different types of disruption to the epithelial tissue (e.g., different patterns). The feedback may also be customized according to different training or calibration modes. By collecting data from repeated use of the example system 500, the processing system 540 can provide statistical data reflecting performance trends for a practitioner over time or comparing performances between practitioners, clinics, sites, etc.

Advantageously, the example system 500 provides an effective tool for practitioner training that allows precise and accurate results to be achieved with consistency. Correspondingly, variability in treatment safety and efficacy profiles is reduced. The example system 500 may be employed to calibrate technique prior to clinical trials or treatments of patients. The example system 500 may also be employed to investigate aspects of different techniques (e.g., in clinical or pre-clinical models), which may involve evaluating different applicators and/or applying applicators according to different parameters, such as pressures, number of strokes, length of strokes, stroke directions, etc.

The example system 500 quantifies aspects of a manual procedure for standardized evaluation and/or optimization. Although the example system 500 is disclosed in connection with treatments involving the disruption of epithelial tissue, similar systems may be employed to evaluate and/or optimize other manual techniques by quantifying aspects of the techniques to provide feedback that can standardize performance.

The use of riboflavin as the cross-linking agent and UV light as the photo-activating light in the embodiments above is described for illustrative purposes only. In general, other types of cross-linking agents may be alternatively or additionally employed according to aspects of the present disclosure. Thus, for example Rose Bengal (4,5,6,7-tetrachloro-2',4',5',7'-tetraiodofluorescein) may be employed as a cross-linking agent. Rose Bengal has been approved for application to the eye as a stain to identify damage to conjunctival and corneal cells. However, Rose Bengal can also initiate cross-linking activity within corneal collagen to stabilize the corneal tissue and improve its biomechanical strength. Like Riboflavin, photoactivating light may be applied to initiate cross-linking activity by causing the Rose Bengal to general oxygen and/or other radicals in the corneal tissue. The photoactivating light may include, for example, UV light or green light. The photoactivating light, for instance, may include photons having energy levels sufficient to individually convert $O_2$ into singlet oxygen, or may include photons having energy levels sufficient to convert $O_2$ into singlet oxygen in combination with other photons, or any combination thereof.

Although embodiments of the present disclosure may describe stabilizing corneal structure after treatments, such as LASIK surgery, it is understood that aspects of the present disclosure are applicable in any context where it is advantageous to form a stable structure of corneal tissue through cross-linking. Furthermore, while aspects of the present disclosure are described in connection with the re-shaping and/or strengthening of corneal tissue via cross-linking the corneal collagen fibrils, it is specifically noted that the present disclosure is not limited to cross-linking corneal tissue, or even cross-linking of tissue. Aspects of the present disclosure apply generally to the controlled cross-linking of fibrous matter and optionally according to feedback information. The fibrous matter can be collagen fibrils such as found in tissue or can be another organic or inorganic material that is arranged, microscopically, as a plurality of fibrils with the ability to be reshaped by generating cross-links between the fibrils. Similarly, the present disclosure is not limited to a particular type of cross-linking agent or activating element, and it is understood that suitable cross-linking agents and activating elements can be selected according to the particular fibrous material being reshaped and/or strengthened by cross-linking. Furthermore, aspects of the present disclosure can be employed to monitor any type of photoactive marker and are not limited to cross-linking agents.

As described above, according to some aspects of the present disclosure, some or all of the steps of the above-described and illustrated procedures can be automated or guided under the control of a controller (e.g., the controller 120). Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the example embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

What is claimed is:

1. A system for enhancing permeability of an epithelium of a cornea, comprising:
    a shaft having a proximal end and a distal end;
    a base disposed at the distal end of the shaft;
    a disruption element coupled to the base, the disruption element including a disruption surface configured to contact the cornea and disrupt an area of the cornea;
    a biasing element configured to apply a biasing force against the disruption element into the contact with the cornea; and
    a guide configured to engage the base and guide two-dimensional movement of the disruption element when the disruption surface contacts the cornea, the two-dimensional movement including lateral translation of the disruption element over the cornea,
    wherein in response to movement of the disruption element on the cornea, the disruption element is configured to disrupt the area of the cornea for partial epithelial disruption, including disruption of apical layers of superficial squamous cells of the cornea.

2. The system of claim 1, wherein the disruption surface includes a pattern of micro-teeth.

3. The system of claim 1, wherein the disruption element includes a sponge material.

4. The system of claim 1, wherein the biasing element is a constant force spring.

5. The system of claim 1, further comprising an applicator for applying a cross-linking agent to the disrupted area of the cornea, the cross-linking agent being transmitted through the epithelium of the cornea through the disrupted area at a greater rate relative to non-ablated areas of the cornea.

6. The system of claim 1, wherein the disruption element is configured to disrupt the area of the cornea up to a depth of no greater than approximately 15 μm.

7. The system of claim 1, wherein the disruption element is configured to disrupt the area of the cornea up to a depth of no greater than approximately 25 μm.

8. The system of claim 1, wherein the base is configured to move along one or more sides of the guide.

9. The system of claim 1, wherein the guide includes an opening and the base is configured to be positioned in the opening such that the base is configured to be guided along an inner edge of the opening.

10. The system of claim 9, wherein the opening is circular and the base is configured to move in a circle defined by the opening.

11. The system of claim 1, wherein the base includes teeth that are configured to engage corresponding teeth of the guide.

12. A system for enhancing permeability of an epithelium of a cornea, comprising:
a housing;
a shaft having a proximal end and a distal end, the shaft coupled to the housing at the proximal end and extending from the housing;
a disruption element coupled to the shaft at the distal end, the disruption element including a disruption surface configured to contact the cornea and disrupt an area of the cornea; and
a biasing element disposed between the housing and the disruption element, the biasing element applying a biasing force against the disruption element into the contact with the cornea,
wherein in response to movement of the disruption element on the cornea, the disruption element is configured to disrupt the area of the cornea for partial epithelial disruption, including disruption of apical layers of superficial squamous cells of the cornea,
wherein the shaft is coupled to the housing via a torsion spring and the shaft is configured to rotate relative to the spring in a first direction against the torsion spring, the system further comprising a lever that prevents the shaft from rotating in a second direction opposite to the first direction in response to rotative force from the torsion spring, the lever being releasable to allow rotation of the shaft in the second direction, the rotation of the shaft in the second direction allowing the disruption element to disrupt the area of the cornea.

13. The system of claim 12, wherein the disruption surface includes a pattern of micro-teeth.

14. The system of claim 12, wherein the disruption element includes a sponge material.

15. The system of claim 12, wherein the biasing element is a constant force spring.

16. The system of claim 12, further comprising an applicator for applying a cross-linking agent to the disrupted area of the cornea, the cross-linking agent being transmitted through the epithelium of the cornea through the disrupted area at a greater rate relative to non-ablated areas of the cornea.

17. The system of claim 12, wherein the disruption element is configured to disrupt the area of the cornea up to a depth of no greater than approximately 15 μm.

18. The system of claim 12, wherein the disruption element is configured to disrupt the area of the cornea up to a depth of no greater than approximately 25 μm.

* * * * *